United States Patent [19]

Lloyd

[11] Patent Number: 4,567,142

[45] Date of Patent: * Jan. 28, 1986

[54] PROCESS FOR ISOMERIZING GLUCOSE

[75] Inventor: Norman E. Lloyd, Ridgefield, Conn.

[73] Assignee: Nabisco Brands, Inc., Parsippany, N.J.

[*] Notice: The portion of the term of this patent subsequent to Oct. 25, 2000 has been disclaimed.

[21] Appl. No.: 544,894

[22] Filed: Oct. 24, 1983

Related U.S. Application Data

[63] Continuation-in-part of Ser. No. 393,845, Jun. 30, 1982, Pat. No. 4,411,996.

[51] Int. Cl.$^4$ .............................................. C12P 19/24
[52] U.S. Cl. .............................................................. 435/94
[58] Field of Search ............................................. 435/94

[56] References Cited

U.S. PATENT DOCUMENTS 4,411,996 11/1983 Lloyd ................................... 435/94

*Primary Examiner*—Lionel M. Shapiro
*Attorney, Agent, or Firm*—Richard Kornutik

[57] ABSTRACT

Glucose is enzymatically isomerized to fructose at a temperature of from about 90° C. to about 140° C. by contact with chemically stabilized glucose isomerase.

40 Claims, No Drawings

PROCESS FOR ISOMERIZING GLUCOSE

CROSS REFERENCE TO RELATED APPLICATIONS

This application is a continuation-in-part of U.S. Ser. No. 393,845 filed June 30, 1982, now U.S. Pat. No. 4,411,996 entitled "Process for Isomerizing Glucose".

This invention relates to enzymatic processes for converting glucose (dextrose) to fructose (levulose).

Most food grade glucose is provided as an enzymatic hydrolysate of corn starch, i.e., the corn syrup of commerce. Glucose is generally rated at being 60 to 80% as sweet as sucrose and therefore sells at a correspondingly lower price. It has long been known to isomerize glucose to fructose (which is even sweeter than sucrose) employing an enzyme having glucose isomerase activity, preferably one which has been immobilized upon an inert support such as diethylaminoethyl-cellulose, porous glass or chitin. Detailed descriptions of the enzymatic conversion of glucose to fructose employing glucose isomerase can be found in Hamilton, et al. "Glucose Isomerase a Case Study of Enzyme-Catalysed Process Technology", *Immobilized Enzymes in Food and Microbial Processes*, Olson et al., Plenum Press, N.Y., (1974), pp. 94–106, 112, 115–137; Antrim, et al., "Glucose Isomerase Production of High-Fructose Syrups", *Applied Biochemistry and Bioenqineering*, Vol. 2, Academic Press (1979); Chen, et al., "Glucose Isomerase (a Review)", *Process Biochem.*, (1980), pp. 30–35; Chen, et al. "Glucose Isomerase (a Review)", *Process Biochem.*, (1980), pp. 36–41; Nordahl, et al., "Fructose Manufacture from Glucose by Immobiled Glucose Isomerase", *Chem. Abstracts*, Vol. 82, (1975), Abs. No. 110316h; and Takasaki, "Fructose Production Glucose Isomerase", *Chem. Abstracts*, Vol. 82, (1975), Abs. No. 110316h; and Takasaki, "Fructose Production by Glucose Isomerase", *Chem. Abstracts*, Vol. 81, (1974), Abs. No. 76474a. In addition, there are numerous patents relating to glucose isomerization of which U.S. Pat. Nos. 3,616,221; Re. 28,885 (originally 3,623,953); 3,694,314; 3,708,397; 3,715,276; 3,788,945; 3,826,714; 3,843,442; 3,909,354; 3,960,663; 4,144,127; and, 4,308,349 are representative.

The levels of fructose achievable by the isomerization of glucose with glucose isomerase is limited by the equilibrium of the isomerization reaction. At 65° C., the equilibrium of the reaction stands at approximately 51% fructose by weight from a starting substrate of pure dextrose. When refined glucose liquor is used as the substrate (containing up to about 6% nonmonosaccharides by weight) and allowing for a reasonable residence time in the enzyme reactor, a 48–52% fructose syrup is the highest fructose content which can be obtained (on a dry basis) by the prior procedures referred to. To attain syrups of higher fructose content, fractionation systems must be employed which add greatly to the cost of the final product. At higher temperatures, however, the equilibrium becomes more favorable. For example, an enzymatic glucose isomerase process capable of being operated at temperatures of from about 90°–140° C. could be used to directly provide high fructose corn syrups (HFCS) containing 53–60 weight percent fructose on a dry basis thereby eliminating the need for fractionation and recycle. The tendency of known glucose isomerase systems to undergo thermal denaturation with an accompanying sharp reduction in activity has thus far frustrated attempts to utilize higher temperature regimes to force the equilibrium of the isomerization further in favor of fructose. Moreover, glucose and especially fructose are sensitive reducing sugars which have a marked tendency to form unwanted by- products such as psicose, colored products, color precursors, fructose dianhydrides, mannose, tagatose, and acids when heated to the temperatures necessary to isomerize according to this invention.

It has now been surprisingly discovered that by carrying out a glucose isomerization procedure within certain critical limits of pH and residence time in an enzyme reactor as hereinafter defined, isomerization temperatures of from about 90° C. to about 140° C. can be effectively utilized to directly provide HFCS syrups of high quality, (i.e., with acceptable by-product formation) containing from about 52 to about 60 weight percent fructose thereby eliminating the need for expensive and operationally complex fractionation and recycle operations which are required by known glucose isomerization processes to achieve the aforesaid range of fructose content.

In accordance with the present invention, glucose is isomerized to fructose by the process which comprises contacting a glucose-containing liquor with chemically stabilized glucose isomerase at a temperature of from about 90° C. to about 140° C. at a pH of from about 3 to about 8 and a contact time sufficient to attain a final content in said liquor of at least about 53 to about 60 weight percent of fructose based on the total carbohydrate content with no substantial formation of psicose, and/or non-fructose, non-glucose sugars.

The glucose which is isomerized to fructose in accordance with the present invention can be derived from any of the known sources for this sugar. For reasons of economy, the glucose will usually be derived from the hydrolysis of cellulose or starch employing acid and/or enzyme , preferably the latter, in accordance with known procedures. Glucose containing liquors obtained in this way will typically contain minor quantities of polysaccharides, sugar oligomers, etc., depending upon the carbohydrate source employed and the hydrolysis method utilized. Cereal grains such as corn, milo, wheat, rye, and the like, and amylaceous roots and tubers such as potatoes, yams, carrots, cassava (manioc), and the like, are excellent sources of starch for conversion to the glucose starting material of this invention. In the United States, corn starch is especially preferred due to its comparatively low cost and ready availability. Since the production of food grade glucose favors the use of enzymatic starch hydrolysis procedures, such procedures are preferred herein. Enzyme hydrolysis methods are described in U.S. Pat. Nos. 4,017,363, 3,912,590, 3,922,196, 3,922,197-201 and 4,284,722, the disclosures of which are incorporated by reference herein.

The glucose isomerase employed herein as the source of enzyme for chemical stabilization can be isolated from among any of the known glucose isomerase-producing microorganisms including *Streptomyces flavorirens, Streptomyces achromogenes, Streptomyces echinatus, Streptomyces albus, Streptomyces wedmorensis, Streptomyces phaeochromogenes, Streptomyces bobiliae, Streptomyces olivochromoqenes, Streptomyces venezuelae, Aerobacter aerogenes, Aerobacter cloacae, Bacillus coagulans, Bacillus megaterium, Bacillus fructosus, Brevibacterium pentaaminoacidicum, Escherichia intermedia, Leuconostoc mesenteroides,* and *Paracolobactrum aerogenoides.* In addition, glucose isomerases elaborated by the genera *Nocardia, Micromonospora, Microbispora, Microellobospora* and *Arthrobacter* can be used. *Streptomyces* sp. ATCC 21,175 is an excellent source for glucose isomerase for use in the process of this invention. As previously stated, it can be advantageous to utilize glucose isomerase which possesses stability at the relatively high isomerization temperatures employed herein, e.g., glucose isomerase produced by *Bacillus stearothermophilus*, in particular, strains selected from the group consisting of *Bacillus stearothermophilus* ATCC 21,365, NRRL B-3680, NRRL B-3681 and NRRL B-3682 as disclosed in U.S. Pat. No. 3,826,714; glucose isomerase produced by a microorganism of the genus *Ampullariella* such as *Ampullariella digitata, Ampullariella lobata, Ampullariella campanulata* and *Ampullariella regularis* (U.S. Pat. No. 4,308,349); glucose isomerase produced by Bacillus licheniformis (European Patent Application No. 41213); and glucose isomerase produced by the thermophiles of the genera described in Japanese Patent Publication No. 74 30588.

In addition to the aforementioned microorganisms, the present invention contemplates the use of mutants and variants thereof as well as genetically transformed microorganisms derived therefrom by introduction of mutated glucose isomerase genes into other microorganisms, including mesophilic and thermophilic microorganisms. The mutated glucose isomerase genes selected for such use are those which provide glucose isomerase which is stable at elevated temperatures, especially above 90° C. and preferably up to about 140° C. Such genes can be prepared by the usual techniques used for mutation of microorganisms such as irradiation or by chemical mutagens. Alternatively, isolated glucose isomerase genes which produce glucose isomerase of moderate thermal stability, as produced for example by certain *Streptomyces* strains, can be mutated *in vitro*. Selection of the appropriate mutated genes is accomplished by reintroduction of the mutated gene into either the parent or other organism, followed by growth and replication of the organism and testing of the thermal stability of the resulting glucose isomerase.

It is also contemplated that recombinant DNA techniques may be used to provide glucose isomerase of improved thermal stability suitable for chemical stabilization and use in this invention. Argos, et al. (Biochemistry 18(25):5698–5703 (1979) point out that certain substitutions of alanyl for glycyl, seryl, valyl and lysyl in enzymes from mesophilic organisms are found in the corresponding enzymes from thermophilic organisms. Perutz (Science, 201, 1187–91 (1978)) indicates that the enzymes of thermophilic bacteria owe their extra stability mostly to additional salt bridges on the protein surface. Zuber (In "Biochemistry of Thermophily", Freidman, S. M., ed., pp. 267–285, Academic Press, N.Y. 1978) provides further information on the structure of thermostable enzymes. Thus if the amino acid sequence and three dimensional (tertiary) structure of a glucose isomerase is known, it is possible to develop improved stability by means of site specific mutations in the isomerase gene to provide enzymes engineered to contain increased amounts of those amino acids that give more stable structures. After the DNA sequence of the glucose isomerase has been determined, a gene synthesizer may be used to generate new sequences, thereby increasing the thermostability of the glucose isomerase produced by such man-made genes. It is contemplated that such engineered enzymes would be especially useful for the practice of this invention.

Since glucose isomerase is produced intracellularly by these and other microorganisms, a source of glucose isomerase can be provided by simply harvesting the cells, and the enzyme can be separated from the cells by techniques known in the art, e.g., cell autolysis, sonic disruption, and employed in an enzyme reactor of known and conventional design. Preferably, the chemically stabilized glucose isomerase can be immobilized on an inert carrier in accordance with known and conventional procedures if it is not insolubilized as a consequence of chemical stabilization. Materials and procedures used for the immobilization of enzymes are well known and are described in a number of publications including Wang, et al., *Fermentation & Enzyme Technology*, John Wiley & Sons, Inc., N.Y. (1979), pp. 318–338 and Kirk-Othmer, *Encyclopedia of Chemical Technology*, 3rd Ed., John Wiley & Sons, Inc., N.Y. (1980) Vol. 9 pp. 148–172, the disclosures of which are incorporated by reference herein. The presence of small quantities of cobalt, manganese and magnesium cation and/or water soluble salt of sulfurous acid such as sodium sulfite, sodium bisulfite, magnesium sulfite, and/or magnesium bisulfite as taught in U.S. Re. Pat. No. 28,885 to reduce or inhibit denaturation of the glucose isomerase during operation of the process is also contemplated.

It is necessary that the concentration of carbohydrate in the glucose-containing feed liquor be within the range of from about 20 to about 85, and preferably from about 30 to about 50, weight percent if the desired results are to be achieved.

It is also necessary that the isomerization be carried out at a pH within the range of from about 3 to about 8 more preferably within the range of from about 4 to about 7 and most preferably between 5 and 6.5. Operation of the isomerization significantly below or above the aforestated pH range will lead to the formation of excessive quantities of undesirable by-products such as psicose, organic acids, colored products, color precursors, fructose dianhydrides and the like.

It has been discovered that the pH for optimum activity of glucose isomerase decreases markedly at high temperatures. Thus, for the glucose isomerase from *Streptomyces rubigenosus*, the activity optimum is pH 8.6–9.2 at 25° C., pH 6.9–7.5 at 75° C. and 5.6–6.2 at 125° C. Thus, as isomerization temperature is increased, the pH of isomerization may be decreased to maintain maximum enzyme activity and additionally, to avoid undue by-product formation.

Yet another necessary requirement of the present invention lies in the duration of contact of the glucose-containing feed liquor and the chemically stabilized glucose isomerase. Such contact must be maintained within the range of from about one second to about 5 hours, preferably from about 30 seconds to about one hour and most preferably from about two minutes to about 30 minutes to provide fructose syrup of acceptable quality.

The preferred contact time between the chemically stabilized glucose isomerase and the glucose containing liquor depends to a large extent upon the pH at which the isomerization reaction is conducted. At the lower end of the pH range, longer contact time can be tolerated without causing undue degradation of glucose and fructose through formation of psicose and other undesirable degradation products. At the upper end of the range, shorter contact time is necessary to avoid psicose and color formation. In practice, the total time the glucose containing syrup is at or near the final reaction temperature is reckoned as the degradation time ($t_d$) since the sugar degradation reactions which occur are nonenzymatic and take place whether or not the liquor is in contact with the glucose isomerase. Degradation time ($t_d$) includes the actual contact time ($T_a$) during which the enzyme and substrate are in contact plus any manipulative time, e.g, entering or leaving the reactor, that the substrate is at or near the reaction temperature. The actual contact time ($t_a$) is the time during which the enzyme is reactively in contact with the substrate, i.e., the direct contact of substrate with the enzyme. Therefore, in conducting isomerizations above 90° C. it is important to minimize the time required to bring the glucose liquor to the desired isomerization temperature (as for example, by mixing the liquor with steam just before or during contact with the isomerase) and once the desired fructose level has been achieved to thereafter rapidly separate the liquor from any active isomerase and then cool the liquor as quickly as possible to less than 90° C. and preferably to less than 70° C.

Therefore, in order to obtain syrup products of acceptable properties without undue degradation of fructose or glucose, the degradation time should be controlled in accordance with the following equation:

$$t_d = a \log(4300/(T+273) - pH - 3.23)$$

in which $t_d$ is the degradation time in minutes; T is the reaction temperature in ° C.; and pH is the pH value of the reaction mixture during the period the mixture is at the reaction temperature.

The above equation shows that shorter effective contact times are required at higher temperatures and/or higher pH values. The pH to be used for the reaction will usually be at or near the optimum pH for the selected isomerase. The temperature (T) can be adjusted according to the composition of the substrate and the fructose content desired as discussed hereinafter. These relationships are provided, for example, in equations 5, 6 and 7.

Further control of contact time can be provided using the relationship shown in equation 4 which shows that contact time is inversely proportional to the enzyme activity. Therefore, for an isomerase with optimum pH of 6.0 and a reaction temperature of 110° C., the degradation time should be controlled to about 100 minutes or less.

If a soluble form of chemically stabilized glucose isomerase is used it will be necessary to inactivate such (as for example, by pH reduction to a range that will inactivate the isomerase) before the cooling step to avoid any reconversion to glucose of the fructose formed during the high temperature isomerization step since the isomerization reaction is, of course, reversible.

The maximum degree of conversion of glucose to fructose that can be attained is governed by the thermodynamic equilibrium between glucose and fructose which in turn is dependent upon the temperature at which the isomerization is conducted. Very careful analysis of equilibrium mixtures of glucose and fructose has established the following relationship.

$$F = 100 K/(K + 1) \tag{1}$$

$$\ln K = -\frac{755}{T + 273} + 2.3005 \tag{3}$$

where F is the % fructose at equilibrium based on total weight of glucose and fructose, T is the temperature (°C.) at which isomerization is conducted, and K=glucose over fructose equilibrium constant.

Actual contact time between the glucose containing syrup and isomerase in a reactor can generally be reckoned by reference to the following formula when a reactor containing an immobilized form of isomerase is used.

$$t_a = \frac{CV \ln\left[\dfrac{F_e - F_o}{F_e - F}\right]}{kA} \tag{4}$$

where
- $t_a$ = the actual contact time
- C = concentration of glucose and fructose
- V = The free volume of fluid in the reactor (volume of reaction mixture minus the volume occupied by the immobilized enzyme particles)
- $F_e$ = fraction of fructose in the glucose/fructose mixture at equilibrium when at the isomerization temperature
- $F_o$ = fraction of fructose (based on G+F) at the entrance to the reaction mixture
- F = fraction of fructose (based on G+F) in the solution exiting the reaction mixture
- k = reaction rate constant for isomerization at the isomerization conditions
- A = activity of isomerase in the reaction mixture Values of k for immobilized isomerase prepared according to the examples following, range from about 0.07 to about 5 g hr$^{-1}$ IGIU$^{-1}$ at temperatures from 90° C. to 140° C. respectively. This relationship shows the need to minimize contact time at high temperature by using packed beds of high activity per unit volume. Packed beds formed according to the procedures in the following examples can contain up to 2000 IGIU/ml which can result in attainment of 99.5% of equilibrium fructose content in less than one minute in a high temperature reactor when staged reactors are used at different temperatures and the feed to a first reactor is isomerized at low temperature before isomerizing at high temperature in a second reactor. When utilizing a staged reactor system is is preferred to employ a process for enzymatically converting glucose to fructose which comprises contacting a glucose-containing feed liquor containing from about 20 to about 85 weight percent glucose with glucose isomerase at a temperature of from about 20° C. to about 80° C. at a pH of about 6.0 to 9.0 and a contact time of about 0.5 to about 2 hours to convert from 40 to about 45 weight percent of the glucose present in said liquor to fructose, increasing the temperature of the isomerization medium to from about 90° C. to about 140° C., adjusting the pH of the isomerization medium as necessary to within the range of from about 3 to about 8, contacting the fructose-containing liquor with the glucose isomerase for an additional period of from about one second to about 5 hours to increase the conversion level to from about 53 to about 60 weight percent of the glucose present in the original glucose-containing feed liquor, there being no substantial formation of psicose or other non-fructose, non-glucose sugars. Therefore, use of high potency packed beds can lead to very low effective contact times which in turn minimizes the degradation of fructose which occurs at the high temperatures required for this invention.

In the selection of glucose isomerase immobilization techniques, it is preferred that methods capable of yielding small, substantially non-compressable, porous catalyst particles be used so that inhibition of isomerization rate diffusion effects will be mimimized. Alternatively, the isomerase may be immobilized in the pores of a membrane through which the glucose solution is forced during high temperature isomerization as a means of promoting good contact between enzyme and substrate minimizing diffusional limitations. The support used for immobilization is preferably totally insoluble and inert in order to avoid undue contamination or degradation of the glucose/fructose components of the substrate solutions.

In commercial practice, however, fructose containing syrups are not manufactured from pure glucose. Rather, starch hydrolysates (as prepared in the above mentioned references) are used as the glucose source and these invariably contain non-glucose and non-fructose saccharides (hereinafter referred to as polysaccharides) derived from incomplete hydrolysis of starch, and the reversion of glucose. Typically these constitute from 3% to 8% of the total dry weight as the saccharides derived by starch hydrolysis. It is therefore necessary when reckoning the temperature at which isomerization is to be conducted to allow for any polysaccharide contained in the glucose liquor as well as other factors such as the total dry basis fructose content to be attained, formation of psicose and other nonglucose and nonfructose products during the effective contact time of the glucose liquor and the isomerase. Relationships for the calculation of isomerization temperature are shown below:

$$T = \frac{755}{2.3005 - \ln K} - 273 \quad (5)$$

$$K = \frac{F}{100 - F} \quad (6)$$

$$F = \frac{10,000 \, (M + C)}{Q \, (100 - P)} \quad (7)$$

$T$ = isomerization temperature (°C.)
$F$ = equilibrium fructose content (% based on total glucose + fructose) at temperature $T$.
$M$ = % fructose dry basis required in the isomerized product.
$C$ = % psicose + other degradation products formed during the effective isomerization contact time.
$Q$ = % of equilibrium attained during isomerized reaction.
$P$ = % polysaccharide content of glucose liquor.

Typically, less than 1% and preferably less than 0.5% psicose and other degradation products will be formed and 99.5% of equilibrium can be attained. Therefore, to prepare syrups with 55.5% fructose (dry basis), the following isomerization temperatures are required for glucose liquors of the indicated polysaccharide contents.

| Polysaccharide in Glucose liquor (% dry basis) | Isomerization Temperature (°C.) |
|---|---|
| 0 | 95.7 |
| 1 | 99.1 |
| 2 | 104.3 |
| 3 | 108.9 |
| 4 | 113.8 |
| 6 | 124.3 |

-continued

| Polysaccharide in Glucose liquor (% dry basis) | Isomerization Temperature (°C.) |
|---|---|
| 8 | 136.1 |

The accepted article of commerce contains on the average, 55.5% fructose on a dry basis. This is so because at this fructose level, high fructose corn syrup (HFCS) attains equal sweetness with sucrose on a weight for weight dry basis. Moreover, HFCS of 55.5% fructose content is firmly established as the article of commerce that is used interchangably as a total or partial replacement for sucrose in many food products and especially in carbonated soft drinks. Consumption of this type of HFCS in the U.S. is expected to be 2.9 billion pounds in 1982 with growth to 4.0 billion pounds in 1983. Owing to the complexities inherent in delivering, storing, metering and formulating HFCS into food products, there is a universal demand for uniformity of product from one HFCS manufacturer to another so that product from different supply sources can be used interchangably and simultaneously. Therefore, fructose level of 55–56% dry basis has attained special significance as a target level in the technology associated with HFCS manufacture.

The present process provides fructose levels of at least 53%, preferably at least 54% and most preferably at least 55%.

As desired, in lieu of employing a solution containing only glucose as the substrate for the present process, it is also feasible to use a solution of glucose in which part of the glucose is already isomerized to fructose. For example, a solution of isomerized glucose containing up to 50% fructose can be treated in accordance with the present process to increase the concentration of fructose to the more desireable levels of above 50%, and the preferred levels of 55–56% and higher.

Solutions of glucose containing fructose in amounts of less than 50% by weight of carbohydrate can be prepared by art recognized procedures.

With the foregoing requirements of glucose concentration, pH and contact time in mind, known glucose isomerization processes can be suitably adapted to operate at from about 90° to about 140° C., preferably between about 100° C. and about 110° C., to provide the high glucose-fructose syrups of this invention.

The thermostability of glucose isomerase may be significantly increased by one or more chemical treatments with the enzyme still retaining an appreciable activity as will be discussed below. Enzyme so treated is termed "chemically stabilized isomerase" for the purpose of this disclosure.

Chemical stabilization of isomerase is effected by a number of different methods which can result in increased thermal stability. The fundamental approach is to introduce structural elements into the enzyme molecule in such a manner that the enzyme will resist unfolding when heated beyond its normal thermal denaturation point. A preferred method for accomplishing this is to modify the enzyme by chemical substitution thereon of moieties containing polymerizable vinyl groups such that the latter are firmly 5 attached to the surface of the enzyme molecule at several points. Thereafter, the modified enzyme is mixed with one or more polymerizable vinyl compounds in aqueous solution and the mixture copolymerized to form the chemically stabilized enzyme wherein the enzyme is firmly bonded at numerous points to a three dimensional polymeric matrix which has formed a structure complemtary in shape to that of the enzyme.

Examples of this type of stabilization are described by Martinek et al. in Biochem. Biophys. Acta 485, 1–12 (1977) and by Kulys et al. in Biokhimiya, 42, No. 3, 453–59 (1978).

It is essential when conducting the above reactions that conditions that can lead to denaturation of the isomerase with consequent loss of activity be avoided. For example, extremes of pH and temperature must be avoided during any and all of the manipulations necessary to carry out the above reactions.

Examples of reagents that are used to modify isomerase to substitute polymerizable vinyl groups thereon are acryloyl chloride, methacryloyl chloride, acrolein, crotonaldehyde, maleic anhydride, 3,4-epoxybutene, acrylic acid-2,3-epoxypropyl ester, acrylic acid-2,3-thioglycidyl ester, 1-allyloxy-3-(N-ethyleneimine)-2-propanol, acrylic acid-0-succinamide ester, chloromaleic acid anhydride, maleic acid azide, 3-bromopropene, and allyl isothiocyanate. Such compounds are capable of reacting with the free amino groups of isomerase, for example, the epsilon-amino group of lysine moieties.

Still other compounds capable of reacting with the free carboxylic acid groups of isomerase may be employed to substitute readily polymerizable vinyl moieties thereon as will be apparent to the skilled artisan.

Examples of vinyl compounds that can be copolymerized with the modified isomerase are sodium acrylate, sodium methacrylate, acrylamide, hydroxyethyl methacrylate, acryloylpiperidine-4-spiro-2'-(1',3'-dioxacrylopentane), 1-acryloyl-4-piperidone, and acryloylmethoxyamine. Generally, water soluble monomers or monomer mixtures that will result in water soluble polymers (if polymerized in the absence of crosslinking agents) are preferred.

Typically, difunctional vinyl compounds are included in the monomer mixture (0.1–5% of the total monomer) to provide crosslinking sites which lead to a three dimensional polymer network. Suitable compounds are N,N'-methylene-bis-acrylamide and ethylene glycol dimethacrylate. When these are used, the polymerized mixture forms an insoluble gel which results in immobilization of the isomerase.

Initiation systems commonly used in vinyl polymerizations are suitable such as ammonium persulfate plus sodium bisulfite, hydrogen peroxide plus ferrous sulfate, potassium sulfate plus N,N,N',N'-tetramethylethylenediamine, and riboflavin (plus light).

Alternatively, noncovalent bonding to the three dimensional polymer matrix may be sufficient to confer the desired rigidity to the isomerase molecule and thereby effect a significant increase in thermostability. This can occur when isomerase is mechanically entrapped within a crosslinked polymeric gel. In this case, it is not necessary that the isomerase be modified by attachment of a vinyl compound thereto prior to the polymerization step. However, concentration of the gel must be greater than about 30% by weight before significant stabilization occurs and gels of about 50% concentration are preferred. Monomers capable of giving polymer gels that can form electrostatic and hydrogen bonds with the isomerase are required as, for example, sodium acrylate, sodium methacrylate, acrylamide, and hydroxyethylmethacrylate.

Examples of stabilization by incorporation into gels are given by Martinek et al. in Biochem. Biophys. Acta 485, 13–28 (1977) and by Kulys et al. in J. Solid Phase Biochem., 3, 95–105 (1978).

A third method of isomerase rigidification is intramolecular crosslinking which is capable of conferring added thermostability.

Examples of such stabilization are discussed by Torchilin et al. in Biochem. Biophys. Acta, 522, 277–283 (1978), Martinek et al. in J. Solid Phase Biochem, 2, 343–85 (1977) and Torchilin et al. in Biochem. Biophys. Acta, 568, 1–10 (1979).

Suitable crosslinking agents for use in the present invention include difunctional compounds which are capable of reacting with pendant functional groups on the enzyme molecule. Most commonly, such functional groups are amino groups, generally primary amino groups which can react with a wide variety of functional groups such as carboxylic acid, sulfonyl halide, aldehydes, isocyanates, propiolates, and the like.

Thus, the crosslinking agents include dicarboxylic acid anhydrides such as succinic anhydride and adipic anhydride; the corresponding dialdehydes such as glyoxal, succinaldehyde and glutaraldehyde; unsaturated compounds such as acrolein and crotonaldehyde, diol propiolates such as ethylene glycol bispropiolate, propylene glycol bispropiolate and hexamethylene glycol bispropiolate; and disulfonyl halides such as benzene-1,3-disulfonyl chloride; naphthalene-1,5-disulfonyl chloride and tolyl-2,4-disulfonyl chloride.

In addition, since the enzyme contains or can be made to contain acid groups reactive with amines, then difunctional amines can be used as crosslinking agents for the present invention. These include, for example, diamines containing up to 12 carbon atoms e.g, phenylenediamine, butylenediamine, hexylenediamine, octylenediamine, pentylenediamine, ethylenediamine and dodecylenediamine.

The amount of crosslinking agent can vary considerably, the ratio of enzyme to crosslinking agent ranging from about 0.1 to about 0.0001. The method of effecting the requisite bonding will be determined to a certain degree by the nature of the selected crosslinking agent and the enzyme. In general, the reagents will be dissolved in a suitable inert solvent medium and the reaction should proceed at reasonably low temperatures to avoid adverse affects on the enzyme which can be sensitive to high temperatures. Usually, reactions at or near room temperature are preferred and water or aqueous solvents are used as reaction medium.

In addition to substituting polymerizable vinyl groups on the enzyme molecule and thereafter polymerizing by the previously described methods, a further embodiment involves condensing a preformed polymer with the isomerase by formation of intermolecular covalent bonds to form a stabilized molecule. For example, polypeptides, such as naturally occurring proteins and hydrolysis products thereof, can be reacted using known techniques for peptide linkage formation with glucose isomerase to form stabilized enzyme. The products so produced may be water-soluble but can be rendered water-insoluble using crosslinking agents such as glutaraldehyde and the resulting crosslinked enzyme system is usually even more stable. The peptide formation reactions are accomplished by known methods, e.g., by use of carbodiimides.

As desired, the inital enzyme may be derivatized to insert desired functionality into the molecule for the purpose of the condensation with the preformed molecule. Thus, for carboxy functionality, a free-amino-containing enzyme can be reacted with a dicarboxylic acid to convert to a carboxy-containing enzyme.

The preformed polymers to be used in the foregoing embodiment can be any which contain the requisite type and amount of functional groups, e.g., amino or carboxy, for the intended reactions. Preferred are polypeptides such as natural proteins, e.g., chitosan, yeast protein and the like, as well as mixtures; and amino-containing polymers such as polyethyleneimine. Usually, the preferred preformed polymer form water-soluble products and it is preferred to render these insoluble by reaction with crosslinking agents, e.g, glutaraldehyde and others as previously described.

In all of the foregoing methods of modifying the enzyme, it is essential to ensure that sufficient chemical functionality, e.g., amino or carboxy groups, is present to achieve a significant level of the desired result.

For example, when selecting the preformed polymer to be reacted with the enzyme, it is required that the polymer contain groups reactive with the available groups on the enzyme molecule. Thus, a protein with pendant carboxy groups would be selected for reaction with pendant amino groups of the enzyme. Additionally, there should be a reasonable number of reactive groups on the selected reactants to assure multipoint attachment of the reactants to realize significant stabilization. The determination of the nature and number of such reactive groups for the respective reagents is, of course, well known in the art.

Yet another method whereby the thermostability of enzymes can be increased is to alter the surface structure chemically without causing appreciable loss of activity. Thus, surface amino groups may be amidinated (Ludwig, M. L. and Hunter, M. J., *Meth. Enzymol.* 11, 595-604 (1967)) or guanidinated (Kimmel, J. R., *Meth. Enzymol.* 11, 584-589 (1967)) to form substituents closely resembling arginine. Lactic dehydrogenase and several other proteins have been stabilized (see Tuengler, F. and Pfleiderer, G., *Biochem. Biophys. Acta*, 284, 1-8 (1977); Minotani, N., et al., *Biochim. Biphys. Acta*, 581, 334-341 (1979); and Cupo, P., et al., *J. Biol. Chem.*, 255, 10828-10833 (1980)).

Activity of the soluble isomerase preparation was determined as described by Lloyd et al. in Cereal Chemistry, 49, No. 5, pp. 544-553 (1972). One IGIU is the amount of isomerase that converts 1 micromole of glucose to fructose per minute in a solution containing 2 moles of glucose per liter, 0.02 moles of $MgSO_4$ per liter, and 0.001 moles of $CoCl_2$ per liter at a pH of 6.85 (0.2 M sodium maleate) and a temperature of 60° C. when determined by the above method.

The following examples are further illustrative of the process of this invention.

EXAMPLE 1

This example demonstrates direct isomerization of a glucose containing solution comprised predominantly of a refined corn starch hydrolysate to attain a composition of 55.5% fructose on a dry basis wherein a two stage isomerization process was used. A low temperature isomerization at 70° C. was first conducted with the product of this reaction used as feed to a second high temperature reactor (105.2° C.) containing a chemically stablized isomerase. The chemically stabilized isomerase is one wherein the enzyme is covalently bonded to a soluble polymer and then made insoluble to form an immobilized catalyst.

The hydrolysate was prepared from corn starch by processes as described in U.S. Pat. Nos. 3,644,126 (liquefaction) and 3,280,006 (saccharification). The saccharified liquor was refined according to U.S. Pat. No. 3,834,940 to yield a product containing 95.3% glucose dry basis. Sufficient crystalline glucose was added to bring the total glucose content to 97.6% on a dry basis. The resultant solution had the following composition:

| | |
|---|---|
| Total Dry Substance (%) | 50.2 |
| Glucose (% Dry Basis) | 97.6 |
| Fructose (% Dry Basis) | 0.0 |
| Polysaccharide (% Dry Basis) | 2.4 |
| Psicose (% Dry Basis) | 0.0 |
| $NaHSO_3$ (mM) | 50.0 |
| $MgSO_4$ (mM) | 5.0 |
| $CoCl_2$ (mM) | 0.1 |
| pH | 6.8 |

The low temperature isomerization was conducted at 70° C. by pumping the above substrate solution through the low temperature reactor at a flow rate of 3.2 ml/min. The low temperature (70° C.) isomerase reactor was constructed by packing isomerase immobilized on DEAE-cellulose (prepared according to U.S. Pat. No. 3,788,945) into a 1" diameter glass column equipped with inlet and outlet and with a jacket for the circulation of water from a thermostat. The headspace over the packing contains a thermometer and is otherwise filled with glass beads to minimize dead space as far as practical. The reactor contains enough immobilized isomerase to provide 20,000 IGIU and the packed bed is about 15 cm high. The first 1000 ml exiting the reactor was discarded. The effluent exiting thereafter was collected for use in the second high temperature isomerization.

The chemically stabilized catalyst used in high temperature reactor was prepared in the following manner.

A species of *Streptomyces rubigenosus* derived from *S. rubinqenosus* ATCC 21175 was grown by submerged aerobic fermentation on a medium of the following composition:

| | % by Weight |
|---|---|
| Dextrose | 9.0 |
| Corn steep Liquor (Solids) | 1.6 |
| Diammonium Phosphate | 0.08 |
| Manganese Sulfate | 0.06 |
| Antifoam (Pluronic PL-61) | 0.003 |

The medium was sterilized at 121° C. for 45 min., cooled and adjusted to pH 6.8-7.0. It was inoculated with 14% (v/v) of an inocula comprising the contents of a seed fermentor prepared with the *S. rubigenous* variant mentioned above. Fermentation was conducted under aseptic conditions at 30° C. for about 60 hours with aeration at 0.65 vvm. *S. rubigenosus* ATCC 21175 can also be used for inoculation and production of isomerase in which case media of the following composition is used.

| | % by Weight |
|---|---|
| Dextrose | 0.24 |
| Corn Steep Liquor (solids) | 1.5 |
| Sorbitol | 1.6 |

-continued

|  | % by Weight |
|---|---|
| Cobatous chloride | 0.02 |
| Diammonium Phosphate | 0.56 |
| Xylose | 1.0 |

Glucose isomerase was extracted from the *S. rubigenosus* by adding 0.35% Maquat MC 1412 (Mason Chemical Co.), and 10 ppm of hen's egg lysozyme and agitating for 5 hrs. at 40° C., pH 6.3–6.6. The mixture was then filtered to provide a soltuion of crude, unpurified glucose isomerase.

The crude isomerase was purified by adsorption on DEAE-cellulose (made according to U.S. Pat. No. 3,823,133), filtering and washing the adsorbed product with 0.1 M NaCl solution to remove impurities and then desorbing the isomerase by contacting with 0.45 M NaCl solution. The pH of all solutions was maintained at 7.5 during the purification steps. The solution of partially purified isomerase obtained thereby was mixed with 3 volumes of 95% ethanol at 0° C. to precipitate the isomerase. Perlite filter aid was added, the solids recovered by filtration and air dried to provide a soluble isomerase preparation containing 2500 IGIU/g.

The purified isomerase was dissolved in 1 mM $MnCl_2$ to provide a solution containing 10 mg isomerase per ml at room temperature and the mixture filtered to remove filter aid. The specific activity of this preparation was 37.3 IGIU/mg of protein.

A solution of a soluble polyamine polymer was obtained by dissolving 39.0 g chitosan (Kytex from Hercules Inc., Wilmington, Del. 19899) in 13 L of 0.08 N HCl. Once dissolved, the chitosan solution was made 0.5 M in NaCl by the addition of 380 g of NaCl and the resultant solution was adjusted to pH 6.15 with 8 N NaOH. Finally, the chitosan solution was filtered through a Whatman #3 paper filter to remove insoluble material. To the 13 L of 0.3% chitosan in 0.5 M NaCl at pH 6.15 was added the following: 100 ml of soluble isomerase containing 100,000 IGIU of activity, 197.6 g xylitol (from Sigma Chemical Co.), and 0.619 g of $CoCl_2 \cdot 6H_2O$. This solution was stirred for 2 hr. after which 6.24 g of 1-ethyl-3-dimethylaminopropylcarbodiimide (from Sigma Chemical Co.) was added to covalently bond in a multipoint fashion the carboxyl groups of isomerase to the amino groups of chitosan. After 2 hr. at room temperature, 15.6 ml of a 50% (w/w) glutaraldehyde solution (from Eastman Kodak) adjusted to pH 6.0 with 8N NaOH was added to the reaction to insolubilize the covalently bonded isomerase-chitosan complex. After 15 min. 2 L of a 1 M phosphate solution at pH 8.0 was added to facilitate fracturing of the gel after being formed by the glutaraldehyde addition. The resultant insolubilized isomerase-chitosan was washed with deionized water while on a Buchner vacuum filter. This preparation was then allowed to air dry overnight at room temperature, and was ground and sieved to a 12–60 mesh range. The dry catalyst had an expressed activity of 384 IGIU/g.

The 105.2° C. reactor was prepared in the following manner. A 13 g portion of the catalyst was suspended in substrate and deaerated under laboratory vacuum at room temperature for 60 minutes. The deaerated slurry was used to prepare a 1.5×20 cm bed in a jacketed glass column. The packed bed contained 4992 IGIU.

Substrate prepared from the first stage 70° C. isomerization was adjusted to pH 6.75 and diluted to 42.0% dry substance. This substrate was then pumped through the high temperature reactor column under a pressure of 10 psig and at a flow rate of 1.96 ml/min. at 60° C. for 30 minutes. Temperature within the column was monitored with a thermometer situated directly above the bed, and surrounded by 0.5 cm glass beads to minimize dead volume as far as possible. The column temperature was then rapidly increased by circulating oil from a 106° C. thermostated bath through the jacket.

The effluent from the column was monitored with a recording polarimeter calibrated to read from 50 to 58% fructose. After the column temperature had reached 105.2° C. and when the fructose content of the effluent had reached the desired level, the effluent was collected and immediately cooled in an ice bath. The pH was adjusted to 4.90 by the addition of 1 M citric acid. Effluent was collected until the apparent fructose level dropped below 55%.

Isomerized solutions obtained from the 70° C. and the 105.2° C. reactors were analyzed for carbohydrate composition and color and the results were compared with like analysis conducted on the unisomerized substrate solution as shown in the following table.

TABLE 1

| COMPOSITION OF SUBSTRATE SOLUTIONS ISOMERIZED AT 70° C. and 105.2° C. | | | | | |
|---|---|---|---|---|---|
| | Carbohydrate Composition (% by weight on an ash free dry basis) | | | | |
| Solution Treatment | Fructose | Glucose | Psicose | Polysaccharide | Color (CIRF X100) |
| Unisomerized | 0 | 97.6 | 0 | 2.4 | 0.5 |
| Isomerized at 70° C. | 51.3 | 46.4 | 0 | 2.3 | 0.7 |
| Isomerized at 105.2° C. | 55.5 | 41.6 | 0.3 | 2.6 | 14.1 |

The results show that 55.5% fructose was attained while maintaining psicose below 0.4% by weight dry basis and color <20 (CIRFX100).

EXAMPLE 2

This example illustrates the direct isomerization of a glucose containing solution (comprising a refined corn starch hydrolysate plus crystalline glucose) at high temperature to attain a composition containing 55.2% fructose on a dry basis wherein a two stage isomerization is used with the second stage employing a chemically stabilized isomerase composed of glucose isomerase complexed with polyethyleneimine with the complex rendered insoluble by treatment with glutaraldehyde.

Preparation of Stabilized Isomerase

A soluble glucose isomerase was prepared as described in Example 1. The purified isomerase was dissolved in 1 mM $MnCl_2$ to provide a solution containing 9 mg isomerase per ml at room temperature and the mixture was filtered to remove filter aid. Sixty ml of 10% (w/v) PEI-6 (polyethylenimine, M.W. 600, pH 8) (Dow Chemical Co.) and 3 g of xylitol were added to 300 ml of the enzyme solution and the resultant solution stirred for 15 min. Ten ml of 2.5 M glutaraldehyde was added and the mixture stirred at room temperature for 2 hours. The insolubilized enzyme was recovered by filtration, washed with water and dried overnight in a convection oven at 37° C. 12.8 grams of immobilized isomerase containing about 775 IGIU/g were recovered after drying. Twelve grams of the immobilized enzyme were suspended in the substrate, deaeratd under vacuum for 60 min. at room temperature and used to prepare a 1.5 cm diameter high temperature reactor.

Substrate for the reactor was prepared in the first stage of the two stage isomerization as described in Example 1. This substrate had the following composition:

| Total Dry Substance (%) | 42.6 |
|---|---|
| Glucose (% Dry Basis) | 46.4 |
| Fructose (% Dry Basis) | 51.3 |
| Polysaccharide (% Dry Basis) | 2.3 |
| Psicose (% Dry Basis) | 0.0 |
| $NaHSO_3$ (mM) | 0 |
| $MgSO_4$ (mM) | 50 |
| $CoCl_2$ (mM) | 0.1 |
| pH | 6.75 |

The substrate was pumped through the reactor at 60° C. for 45 min. at about 5 ml/min. The column temperature was then increased to 101.6° C. and the flow rate reduced to 2 ml/min. A back pressure of 12 psi was applied to the column to prevent boiling of the substrate. The effluent was monitored with a recording polarimeter calibrated to read from 50% to 58% fructose. Effluent that exceeded 55% fructose was collected in an ice bath and adjusted to pH 4.0 with 1.0 M citric acid.

The effluent from the high temperature reactor, the substrate from the first stage reactor and the original glucose containing solution used as substrate for the first stage reactor were analyzed for carbohydrate composition and color. Results are summarized in the following table.

TABLE 2
COMPOSITIONS OF SOLUTIONS FROM FIRST AND SECOND STAGE ISOMERIZATIONS

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Unisomerized | 0 | 97.6 | 0 | 2.4 | 0.5 |
| Isomerized at 70° C. | 51.3 | 46.4 | 0 | 2.3 | 0.7 |
| Isomerized at 101.6° C. | 55.2 | 42.1 | 0 | 2.7 | 51.7 |

The results show that 55.2% fructose was attained while maintaining the psicose below 0.2% by weight, dry basis.

EXAMPLE 3

This example demonstrates direct isomerization of glucose to 57.2% fructose by a two stage isomerization process wherein the first reactor was at 70° C. and the second (high temperature) reactor was at 110.4° C. The chemically stabilized isomerase used in the high temperature reaction is one wherein the enzyme is covalently bonded to a soluble polymer and then made insoluble to form an immobilized catalyst.

The substrate and its conversion by the first stage reactor at 70° C. has been described in Example 1.

The immobilized catalyst used in the high temperature reactor at 110.4° C. has also been described in Example 1.

The 110.4° C. reactor was prepared in the following manner. A 28.4 g portion of the catalyst was suspended in substrate and deaerated under laboratory vacuum at room temperature for 60 minutes. The deaerated slurry was used to prepare a 2.5×12.4 cm bed in a jacketed glass column. The packed bed contained 10,885 IGIU.

Substrate prepared from the first stage 70° C. isomerization was adjusted to pH 6.47 and diluted to 42.0% dry substance. This substrate was then pumped through the high temperature reactor column under a pressure of 12 psi and at a flow rate of 3.38 ml/min. with the temperature at 60° C. for 30 minutes. Temperature within the column was monitored with thermometer situated directly above the bed and surrounded by 0.3 cm glass beads to minimize dead volume as far as possible. The column temperature was then rapidly increased by circulating an oil from a 111° C. thermostated bath through the jacket.

The effluent from the column was monitored with a recording polarimeter calibrated to read from 50 to 58% fructose. After the column temperature had reached 110.4° C. and when the fructose content of the effluent had reached the desired level, the effluent was collected and immediately cooled in an ice bath. The pH was adjusted to 4.0 by the addition of 1M citric acid.

Isomerized solutions obtained from the 70° C. and the 110.4° C. reactors were analyzed for carbohydrate composition and color and the results were compared with like analysis conducted on the unisomerized substrate solution as shown in the following table.

TABLE 3
COMPOSITIONS OF SUBSTRATE SOLUTIONS ISOMERIZED AT 70° C. and 110.4° C.

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Unisomerized | 0 | 99.2 | 0 | 0.8 | 0.6 |
| Isomerized at 70° C. | 52.3 | 46.9 | 0 | 0.8 | 0.7 |
| Isomerized at 110.4° C. | 57.2 | 41.5 | 0.3 | 1.0 | 19.8 |

The results show that 57.2% fructose was attained while maintaining psicose below 0.4% by weight dry basis and color (CIRFX100) below 20.

EXAMPLE 4

This example demonstrates direct isomerization of a glucose containing solution comprised predominantly of a refined corn starch hydrolysate to attain a composition of 56.3% fructose on a dry basis wherein a two stage isomerization process was used. A low temperature isomerization at 70° C. was first conducted with the product of this reaction used as feed to a second high temperature reactor (103.3° C.) containing a chemically stabilized isomerase. The chemically stabilized isomerase is one wherein the enzyme is co-reacted with a protective protein (such as that derived from yeast).

The low temperature isomerization step, including a description of substrate and experimental conditions is presented in Example 1.

The chemically stabilized glucose isomerase enzyme used in the high temperature reactor was prepared in the following manner. Soluble glucose isomerase for chemical stabilization was prepared and purified by the method described in Example 1. The specific activity of this preparation was about 40 IGIU/mg of protein. A protective protein was obtained from bakers yeast by the following procedure. To 1229 g of bakers yeast wet cake was added 1000 g of water and 500 g of toluene. The mixture was stirred at room temprature overnight then heated to 85° C. and held at that temperature for about 30 min. The mixture was filtered on a Buchner funnel. Nearly all toluene remained with the insoluble cell debris while the aqueous filtrate contained soluble yeast extract. The aqueous filtrate was reduced in volume to 276 g (rotary evaporator, 40° C.) then 41 g of trichloroacetic acid was added with stirring. The precipitated yeast protein was collected then redissolved in 0.1 M sodium phosphate buffer (pH 7.0). After clarification by filtration, the solution was treated with 900 ml (about 3 volumes) of acetone. The precipitate was collected, dissolved in 0.01 M sodium phosphate buffer (pH 7.0), and the resulting solution was dialyzed against 0.01 M sodium phosphate buffer. The resulting product (150 ml) was labeled protective protein obtained from bakers yeast. A 0.6% chitosan solution was prepared by dissolving 24 g chitosan (Kytex from Hercules Inc., Wilmington, Del.) in 4 liters of 0.08 N HCl. The solution was adjusted to pH 6.2 with 8 N NaOH, filtered through Whatman #3 filter paper, then dialyzed against 16 liters of deionized water. Into a 400 ml beaker was placed about 100,000 IGIU of soluble glucose isomerase enzyme (mixed with filter aid), 1 g xylitol, and 100 ml ($\frac{2}{3}$) of the protective protein obtained from bakers yeast. To this mixture was added 2.4 mg $MgSO_4 \cdot 7H_2O$ and 24 microliters of molar cobalt chloride solution. The mixture was filtered to remove filter aid then the solution was concentrated (rotary evaporator, ~40° C.) to near dryness in a 2 liter round bottom flask. To the flask was then added 800 ml of chitosan (pH 6.2). The mixture was then concentrated (rotary evaporator, ~40° C.) to near dryness and 640 microliters of 50% glutaraldehyde solution (pH adjusted to 6.5) was added. The mixture was stored in a cold room overnight. The gel was then removed from the flask and forced through a U.S. #30 mesh screen and oven dried at ~37° C. The dried enzyme preparation was screened to remove fines (U.S. #80 mesh screen) then used (8.9 g of final product) for the high temperature isomerization.

The 103.3° C. reactor was prepared in the following manner. The glucose isomerase preparation above (8.9 g) was suspended in substrate and deaerated under laboratory vacuum at room temperature for about 30 minutes. The deaerated slurry was used to prepare a 1.5×29 cm bed in a jacketed glass column.

Substrate prepared from the first stage 70° C. isomerization was adjusted to pH 6.75 and diluted to 42.0% dry substance. This substrate was then pumped through the high temperature reactor column at a flow rate of about 1½ ml/min. with the temperature at 60° C. for 30 minutes. Temperature within the column was monitored with a thermometer situated directly above the bed, and surrounded by glass beads (0.5 cm diameter) to minimize dead volume. The column temperature was then rapidly increased by circulting an oil from 104° C. thermostated bath through the jacket.

The effluent from the column was monitored with a recording polarimeter calibrated to read from 50 to 58% fructose. Fractions (about 5 ml) were collected until 55% or greater fructose was being produced at which point the experiment was terminated. During sample collection the effluent was immediately cooled in an ice bath and the pH was adjusted to ~4.0 by addition of molar citric acid (0.1 ml) then dilute HCl.

Isomerized solutions obtained from the 70° C. and the 103.3° C. reactors were analyzed for carbohydrate composition and color. Results were compared with like analysis conducted on the unisomerized substrate solution as shown in the following table.

TABLE 4

COMPOSITIONS OF SUBSTRATE SOLUTIONS ISOMERIZED AT 70° C. and 103.3° C.

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Unisomerized | 0 | 97.6 | 0 | 2.4 | 0.5 |
| Isomerized at 70° C. | 51.3 | 46.4 | 0 | 2.3 | 0.7 |
| Isomerized at 103.3° C. | 56.3 | 41.5 | 0.1 | 2.2 | 34.0 |

The results show that 56.3% fructose was attained while maintaining the psicose below 0.2% by weight dry basis.

EXAMPLE 5

This example demonstrates direct isomerization of a glucose containing solution comprised predominantly of a refined corn starch hydrolysate with a low salt concentration to attain a composition of 55.4% fructose on a dry basis wherein a two stage isomerization process was used. A low temperature isomerization at 70° C. was first conducted and the product of this reaction used as feed to a second high temperature reactor (112.6° C.) containing a chemically stablized isomerase. The chemically stabilized isomerase is one wherein the enzyme is covalently bonded to a soluble polymer in a multipoint attachment manner then made insoluble to form an immobilized catalyst.

The hydrolysate was prepared from corn starch by processes as described in U.S. Pat. No. 3,644,126 (liquefaction) and U.S. Pat. No. 3,280,006 (saccharification). The saccharified liquor was refined according to U.S. Pat. No. 3,834,940 to yield a product containing 93.8% glucose dry basis. Sufficient crystalline glucose was added to bring the total glucose content to 96.9% on a dry basis. The resultant solution had the following composition:

| | |
|---|---|
| Total Dry Substance (%) | 50.3 |
| Glucose (% Dry Basis) | 96.9 |
| Fructose (% Dry Basis) | 0.1 |
| Polysaccharide (% Dry Basis) | 3.1 |
| Psicose (% Dry Basis) | 0.0 |
| $NaHSO_3$ (mM) | 2.5 |
| $MgSO_4$ (mM) | 2.5 |
| $CoCl_2$ (mM) | 0.1 |
| pH | 6.8 |

The low temperature isomerization was conducted at 70° C. by pumping the above substrate solution through the low temperature reactor which was described in Example 1 at a flow rate of 2.5 ml/min. The first 1000 ml exiting the reactor was discarded. The effluent exiting thereafter was collected for use in the second high temperature isomerization.

The chemically stabilized catalyst used in the high temperature reactor was prepared in the following manner. Soluble glucose isomerase was prepared and purified by the method described in Example 1. The specific activity of this preparation was about 40 IGIU/mg of protein. A solution of soluble polymer, a polyamine, was obtained by dissolving 48.4 g of chitosan (Kytex from Hercules Inc., Del. 19899) in 15 L of 0.08 N HCl. Once dissolved, the chitosan solution was made 0.5 M in NaCl by the addition of 438 g of NaCl and the resultant solution was adjusted to pH 6.1 with 8 N NaOH. The chitosan solution was then filtered through a Whatman #3 paper filter to remove insoluble material. To the 15 L of 0.3% chitosan in 0.5 M NaCl at pH 6.1 was added the following: 520 ml of soluble isomerase containing about 602,000 IGIU of activity, 236 g xylitol (from Sigma Chemical Co.), and 3.07 g of $MnCl_2 \cdot 4H_2O$. This solution was stirred for 2 hr. after which 7.44 g of 1-ethyl-3-dimethylaminopropylcarbodiimide (from Sigma Chemical Co.) was added to covalently bond in a multipoint fashion the carboxyl groups of isomerase to the amino groups of chitosan. After 2 hr. at room temperature, 15.5 ml of a 50% (w/w) glutaraldehyde solution (from Eastman Kodak Chem. Co.) adjusted to pH 6.0 with 8 N NaOH was added to the reaction to insolubilize the covalently bonded isomerase-chitosan complex. After 15 min. 4 L of a 1 M phosphate solution at pH 8.0 was mixed into the insoluble isomerase-chitosan. The immobilized isomerase-chitosan was washed with deionized water while on a Buchner vacuum filter containing Whatman #3 filter paper. The preparation was air dried, ground and sieved to a 12–60 mesh range. The dry catalyst had an expressed activity of 803 IGIU/g.

The 112.6° C. reactor was prepared in the following manner. A 7.0 g portion of the catalyst was suspended in substrate and deaerated under laboratory vacuum at room temperature for 60 minutes. The deaerated slurry was used to prepare a 1.0×40 cm bed in a jacketed glass column. The packed bed contained 5621 IGIU.

Substrate prepared from the first stage 70° C. isomerization was adjusted to pH 6.55 and diluted with deionized water to 42.0% dry substance which also lowered the salt concentrations to 2.1 mM for $NaHSO_3$ and 2.1 mM for $MgSO_4$. This substrate was then pumped through the high temperature reactor column under a pressure of 12 psig for 10 min. at a flow rate of 8 ml/min. with the temperature at 60.0° C. Temperature with the column was monitored with a thermometer situated directly above the bed, and surrounded by sand up to the temperature scale to minimize dead volume as far as possible. The column temperature was then rapidly increased by circulating an oil from a thermostated bath at about 114° C. The column temperature was increased to 112.6° C. and the flow rate decreased to 1.89 ml/min.

The effluent from the column was monitored with a recording polarimeter calibrated to read from 50 to 58% fructose. After the column temperature had reached 112.6° C. and when the fructose content of the effluent had reached the desired level, the effluent was collected. The pH was immediately adjusted to 4.0 by the addition of 1 M citric acid. Effluent was collected until the apparent fructose level dropped below 55%.

Isomerized solutions obtained from the 70° C. and the 112.6° C. reactors were analyzed for carbohydrate composition and color and the results were compared with like analysis conducted on the unisomerized substrate solution as shown in the following table.

TABLE 5

COMPOSITIONS OF SUBSTRATE SOLUTIONS ISOMERIZED AT 70° C. and 112.6° C.

| Solution Treatment | Carbohydrate Composition (% by weight on an ash free dry basis) | | | | Color (CIRF X100) |
|---|---|---|---|---|---|
| | Fructose | Glucose | Psicose | Polysaccharide | |
| Unisomerized | 0 | 96.9 | 0 | 3.1 | 0 |
| Isomerized at 70° C. | 51.4 | 45.9 | 0 | 2.7 | 0 |
| Isomerized at 112.6° C. | 55.4 | 42.0 | 0.1 | 2.5 | 8.5 |

The results show that 55.4% fructose was attained while maintaining psicose below 0.2% by weight dry basis and color <9 (CIRF×100).

EXAMPLE 6

This example demonstrates direct isomerization of a glucose containing solution comprised predominantly of a refined corn starch hydrolysate with low salts to attain a composition of 54.8% fructose on a dry basis with extremely low psicose [<0.1% and color (<2 CIRF×100)] wherein a two stage isomerization process was used. The first (low temperature) reactor was at 70° C. and the second (high temperature) reactor was at 105.8° C. The chemically stabilized isomerase used in the high temperature reactor is one wherein the enzyme is covalently bonded to a soluble polymer in a multipoint attachment manner then made insoluble to form an immobilized catalyst.

The substrate and its conversion by the first stage reactor at 70° C. was as described in Example 5.

The immobilized catalyst used in the high temperature reactor at 105.8° C. was as described in Example 5.

The 105.8° C. reactor was prepared in the following manner. A 5.63 g portion of the catalyst was suspended in substrate and deaerated under laboratory vacuum at room temperature for 60 minutes. The deaerated slurry was used to prepare a 1.0×32 cm bed in a jacketed glass column. The packed bed contained 4521 IGIU.

Substrate prepared from the first stage 70° C. isomerization was adjusted to pH 6.5 and diluted with deionized water to 42.0% dry substance which also lowered the salt concentration to 2.1 mM for $MgSO_4$ and 2.1 mM for $NaHSO_3$. This substrate was then pumped through the high temperature reactor column under a pressure of 10 psig and at a flow rate of 8 ml/min. for 10 min. with the temperature at 60.0° C. Temperature within the column was monitored with a thermometer situated directly above the bed and surrounded by sand up to the beginning of the temperature scale to minimize dead volume as far as possible. The column temperature was then rapidly increased by circulating an oil from a thermostated bath at about 107° C. through the jacket.

The effluent from the column was monitored with a recording polarimeter calibrated to read from 50 to 58% fructose. After the column temperature had reached 105.8° C. and when the fructose content of the effluent had reached the desired level, the effluent was collected. The pH was immediately adjusted to 4.90 by the addition of 1 M citric acid.

Isomerized solutions from the 70° C. and the 105.8° C. reactors were analyzed for carbohydrate composition and color and the results were compared with like analysis conducted on the unisomerized substrate solution as shown in the following table.

TABLE 6

COMPOSITIONS OF SUBSTRATE SOLUTIONS ISOMERIZED AT 70° C. and 105.8° C.

| Solution Treatment | Carbohydrate Composition (% by weight on an ash free dry basis) | | | | Color (CIRF X100) |
| --- | --- | --- | --- | --- | --- |
| | Fructose | Glucose | Psicose | Polysaccharide | |
| Unisomerized | <0.1 | 96.9 | 0 | 3.1 | 0 |
| Isomerized at 70° C. | 51.4 | 45.9 | 0 | 2.7 | 0 |
| Isomerized at 105.8° C. | 54.8 | 42.3 | <0.1 | 2.8 | 1.8 |

The results show that 54.8% fructose was attained while maintaining psicose below 0.1% by weight dry basis and color (CIRF×100) below 2.

I claim:

1. A process for isomerizing glucose to fructose which comprises contacting a glucose-containing feed liquor with chemically stabilized glucose isomerase at a temperature of from about 90° C. to about 140° C. at a pH of from about 3 to about 8, an actual contact time sufficient to attain a final content in said liquor of at least about 53 to about 60 weight percent of fructose based on the total carbohydrate content while controlling the degradation time at a value equal to less than the value calculated with the formula.

$$t_d = a \log (4300/T+273) - pH - 3.23) \quad (1)$$

in which T is the reaction temperature in ° C.; pH is the pH of the reaction mixture; and $t_d$ is the degradation time in minutes; to preclude substantial formation of psicose and/or other non-fructose, non-glucose sugars.

2. The process of claim 1 wherein the glucose-containing liquor is obtained from the hydrolysis of corn starch.

3. The process of claim 1 wherein the glucose-containing feed liquor is obtained by isomerization of a corn starch hydrolysate to a fructose content of up to about 52% based on the total carbohydrate content.

4. The process of claim 1 wherein the source of the glucose isomerase is a microorganism selected from the group consisting of Streptomyces species, mutants, variants and genetic modifications thereof.

5. The process of claim 1 wherein the source of the glucose isomerase is a microorganism selected from the group consisting of Streptomyces sp. ATCC 21175; mutants, variants, and genetic modifications thereof.

6. The process of claim 1 wherein the source of the glucose isomerase is a microorganism into which a mutated glucose isomerase gene has been introduced said mutated gene providing glucose isomerase of high thermal stability.

7. The process of claim 1 wherein the glucose isomerase is a thermally stable glucose isomerase.

8. The process of claim 7 wherein the thermally stable glucose isomerase is obtained from *Bacillus Stearothermophilus*.

9. The process of claim 7 wherein the thermally stable glucose isomerase is obtained from *Bacillus licheniformis*.

10. The process of claim 7 wherein the thermally stable glucose isomerase is obtained from a thermophile of the genera *Thermoactinomyces, Thermopolyspora, Thermomonospora* or *Pseudonocardia*.

11. The process of claim 7 wherein the thermally stable glucose isomerase is obtained from a microorganism of the genus *Ampullariella*.

12. The process of claim 1 wherein an enzyme denaturation-inhibiting amount of a water soluble salt of sulfurous acid is present in the isomerization medium.

13. The process of claim 1 wherein the glucose-containing feed liquor contains from about 30 to about 50 weight percent carbohydrate.

14. The process of claim 1 wherein the glucose-containing feed liquor is contacted with chemically stabilized glucose isomerase at about 100° C. to about 110° C.

15. The process of claim 1 wherein the pH of the isomerization medium is maintained at about 5 to about 6.5.

16. The process of claim 1 wherein the contact time is from about 2 minutes to about 30 minutes.

17. The process of claim 1 wherein the chemically stabilized glucose isomerase is used in an immobilized form.

18. The process of claim 1 wherein the chemically stabilized glucose isomerase is immobilized upon diethylaminoethyl cellulose.

19. The process of claim 1 wherein the product fructose-glucose syrup is cooled to a temperature below about 80° C.

20. The process of claim 1 wherein the isomerization mixture is cooled to a temperature of from about 20° to about 80° C. after removal of the enzyme from contact with the isomerization mixture.

21. A process for enzymatically converting glucose to fructose which comprises contacting a glucose-containing feed liquor containing from about 20 to about 65 weight percent glucose with glucose isomerase at a temperature of from about 20° C. to 80° C. at a pH of about 6 to 9 and a contact time sufficient to attain a final content in said liquor of at least about 40 to 50 percent of fructose based on the total carbohydrate content; increasing the temperature of the isomerization medium to from about 90° C. to about 130° C.; adjusting the pH of the isomerization medium as necessary to within the range of from about 3 to about 8, contacting the fructose-containing liquor with chemically-stabilized glucose isomerase for an actual contact time sufficient to attain a final content in said liquor of at least about 53 to about 60 weight percent of fructose based on the total carbohydrate content while controlling the degradation time at a value equal to or less than the value calcualted with formula $$t_d = a \log (4300/T=273) - pH - 3.23) \quad (1)$$

in which T is the reaction temperature in ° C.; pH is the pH of the reaction mixture; and $t_d$ is the degradation time in minutes; to preclude substantial formation of psicose and/or other non-fructose, non-glucose sugars.

22. The process of claim 21 wherein the glucose-containing feed liquor is obtained by isomerization of a corn starch hydrolysate to a fructose content of up to about 52% based on the total carbohydrate content.

23. The process of claim 21 wherein the source of the glucose isomerase is a microorganism selected from the group consisting of *Streptomyces* species, mutants, variants and genetic modifications thereof.

24. The process of claim 21 wherein the source of the glucose isomerase is a microorganism selected from the group consisting of *Streptomyces* sp. ATCC 21175; mutants, variants, and genetic modifications thereof.

25. The process of claim 21 wherein the source of the glucose isomerase is a microorganism into which a mutated glucose isomerase gene has been introduced said mutated gene providing glucose isomerase of high thermal stability.

26. The process of claim 21 wherein the glucose isomerase is a thermally stable glucose isomerase.

27. The process of claim 26 wherein the thermally stable glucose isomerase is obtained from *Bacillus Stearothermophilus*.

28. The process of claim 26 wherein the thermally stable glucose isomerase is obtained from *Bacillus licheniformis*.

29. The process of claim 26 wherein the thermally stable glucose isomerase is obtained from a thermophile of the genera *Thermoactinomyces, Thermopolyspora, Thermomonospora* or *Pseudonocardia*.

30. The process of claim 26 wherein the thermally stable glucose isomerase is obtained from a microorganism of the genus *Ampullariella*.

31. The process of claim 21 wherein an enzyme denaturation-inhibiting amount of a water soluble salt of sulfurous acid is present in the isomerization medium.

32. The process of claim 21 wherein the glucose-containing feed liquor contains from about 30 to about 50 weight percent carbohydrate.

33. The process of claim 21 wherein the glucose-containing feed liquor is contacted with chemically stabilized glucose isomerase at about 100° C. to about 110° C.

34. The process of claim 21 wherein the pH of the isomerization medium is maintained at about 5 to about 6.5.

35. The process of claim 21 wherein the contact time is from about 2 minutes to about 30 minutes.

36. The process of claim 21 wherein the chemically stabilized glucose isomerase is used in an immobilized form.

37. The process of claim 21 wherein the chemically stabilized glucose isomerase is immobilized upon diethylaminoethyl cellulose ° C. to about 140° C. by contact with chemically stabilized glucose isomerase.

38. The process of claim 21 wherein the product fructose-glucose syrup is cooled to a temperature below about 80° C.

39. The process of claim 21 wherein the isomerization mixture is cooled to a temperature of from about 20° to about 80° C. after removal of the enzyme from contact with the isomerization mixture.

40. The process of claim 21 wherein the glucose-containing liquor is obtained from the hydrolysis of corn starch.

* * * * *